(12) United States Patent
Seifert (10) Patent No.: US 8,437,864 B2
(45) Date of Patent: May 7, 2013

(54) MEDICAL ELECTRICAL LEAD WITH EMBEDDED ELECTRODE SUB-ASSEMBLY

(75) Inventor: Kevin R. Seifert, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 423 days.

(21) Appl. No.: 12/626,984

(22) Filed: Nov. 30, 2009

(65) Prior Publication Data

US 2010/0137958 A1 Jun. 3, 2010

Related U.S. Application Data

(60) Provisional application No. 61/118,608, filed on Nov. 29, 2008.

(51) Int. Cl.
*A61N 1/00* (2006.01)
(52) U.S. Cl.
USPC .......................................................... 607/116
(58) Field of Classification Search .................. None
See application file for complete search history.

(56) References Cited

U.S. PATENT DOCUMENTS

| | | | | |
|---|---|---|---|---|
| 4,384,083 A | * | 5/1983 | Baker | 525/420.5 |
| 4,481,953 A | | 11/1984 | Gold et al. | |
| 4,603,705 A | | 8/1986 | Speicher et al. | |
| 5,016,646 A | * | 5/1991 | Gotthardt et al. | 607/122 |
| 5,105,826 A | * | 4/1992 | Smits et al. | 607/119 |
| 5,174,288 A | | 12/1992 | Bardy et al. | |
| 5,271,417 A | | 12/1993 | Swanson et al. | |
| 5,522,872 A | | 6/1996 | Hoff | |
| 5,676,694 A | | 10/1997 | Boser et al. | |
| 5,728,149 A | * | 3/1998 | Laske et al. | 607/122 |
| 5,928,277 A | | 7/1999 | Laske et al. | |
| 5,935,159 A | | 8/1999 | Cross, Jr. et al. | |
| 5,957,970 A | | 9/1999 | Shoberg et al. | |
| 6,016,436 A | | 1/2000 | Bischoff et al. | |
| 6,038,463 A | | 3/2000 | Laske et al. | |
| 6,038,472 A | | 3/2000 | Williams et al. | |
| 6,052,625 A | | 4/2000 | Marshall | |
| 6,061,595 A | | 5/2000 | Safarevich | |
| 6,181,971 B1 | | 1/2001 | Doan | |
| 6,256,542 B1 | | 7/2001 | Marshall et al. | |
| 6,259,954 B1 | | 7/2001 | Conger et al. | |
| 6,289,251 B1 | | 9/2001 | Huepenbecker et al. | |
| 6,615,695 B1 | | 9/2003 | Hjelle et al. | |
| 6,697,675 B1 | | 2/2004 | Safarevich et al. | |
| 6,704,604 B2 | | 3/2004 | Soukup et al. | |
| 6,801,809 B2 | | 10/2004 | Laske et al. | |
| 6,813,521 B2 | | 11/2004 | Bischoff et al. | |
| 6,920,361 B2 | | 7/2005 | Williams | |
| 7,031,777 B2 | | 4/2006 | Hine et al. | |
| 7,130,700 B2 | | 10/2006 | Gardeski et al. | |
| 7,277,762 B2 | | 10/2007 | Belden et al. | |

(Continued)

*Primary Examiner* — Christopher D Koharski
*Assistant Examiner* — Nadia Ahmad
(74) *Attorney, Agent, or Firm* — Reed A. Duthler (57) ABSTRACT

A medical electrical lead that includes a lead body and at least one tubular electrode sub-assembly positioned over and attached to the lead body. The lead body includes at least one elongated conductive element, such as a cable, that is electrically connected to a coiled electrode of the tubular electrode sub-assembly. The tubular electrode sub-assembly includes a tubular liner and an electrode embedded in the outer surface of the liner. In some embodiments, only a portion of the inner surface of the tubular liner is attached to the lead body in order to improve flexibility of the medical electrode lead in the area occupied by the tubular electrode sub-assembly.

25 Claims, 7 Drawing Sheets

U.S. PATENT DOCUMENTS

| | | |
|---|---|---|
| 7,474,924 B2 | 1/2009 | Honeck et al. |
| 7,512,447 B2 | 3/2009 | Marshall et al. |
| 2005/0240252 A1 | 10/2005 | Boser et al. |
| 2006/0241734 A1* | 10/2006 | Marshall et al. .............. 607/122 |
| 2007/0276458 A1 | 11/2007 | Boser |
| 2009/0254162 A1 | 10/2009 | Quinci et al. |

* cited by examiner

MEDICAL ELECTRICAL LEAD WITH EMBEDDED ELECTRODE SUB-ASSEMBLY

CROSS-REFERENCE TO RELATED APPLICATIONS

This application claims the benefit of U.S. Provisional Application No. 61/118,608, filed on Nov. 29, 2008. The disclosure of the above application is incorporated herein by reference.

TECHNICAL FIELD

The disclosure relates to implantable medical devices and, more particularly, to implantable medical electrical leads.

BACKGROUND

The human anatomy includes many types of tissues that can either voluntarily or involuntarily, perform certain functions. After disease, injury, or natural defects, certain tissues may no longer operate within general anatomical norms. For example, after disease, injury, time, or combinations thereof, the heart muscle may begin to experience certain failures or deficiencies. Certain failures or deficiencies can be corrected or treated with implantable medical devices (IMDs), such as implantable pacemakers, implantable cardioverter defibrillator (ICD) devices, cardiac resynchronization therapy defibrillator devices, or combinations thereof.

IMDs detect and deliver therapy for a variety of medical conditions in patients. IMDs include implantable pulse generators (IPGs) or implantable cardioverter-defibrillators (ICDs) that deliver electrical stimuli to tissue of a patient. ICDs typically include, inter alia, a control module, a capacitor, and a battery that are housed in a hermetically sealed container with a lead extending therefrom. It is generally known that the hermetically sealed container can be implanted in a selected portion of the anatomical structure, such as in a chest or abdominal wall, and the lead can be inserted through various venous portions so that the tip portion can be positioned at the selected position near or in the muscle group. When therapy is required by a patient, the control module signals the battery to charge the capacitor, which in turn discharges electrical stimuli to tissue of a patient through via electrodes disposed on the lead, e.g., typically near the distal end of the lead. Typically, a medical electrical lead includes a flexible elongated body with one or more insulated elongated conductors. Each conductor electrically couples a sensing and/or a stimulation electrode of the lead to the control module through a connector module.

In the context of implantable defibrillators, most systems include large surface area implantable electrodes to be mounted in or adjacent the heart. One common approach of providing a large surface area electrode is to employ an elongated exposed coil of biocompatible metal. In the context of an endocardial lead, this is disclosed in U.S. Pat. No. 4,161,952 issued to Kinney. In the context of an epicardial lead, this is disclosed in the context of U.S. Pat. No. 4,817,634 issued to Holleman et al.

An elongated coil serving as the electrode is typically mounted around the exterior of an insulative lead body. It is believed desirable in this context to stabilize the electrode coil with respect to the lead body, both to provide mechanical integrity and to prevent fibrous ingrowth around the individual coils of the electrode coil. In the above cited Kinney et al. patent and in U.S. Pat. No. 4,934,049, issued to Keikhafer et al., this is accomplished by sliding the coil over the lead body and backfilling the spaces between the electrode coil with a plastic material. In prior U.S. Pat. No. 5,042,143 issued to Holleman, et al. and U.S. Pat. No. 5,344,708 issued to Bischoff, et al. alternative methods of producing a lead structure similar to that produced in the Keikhafer patent are disclosed. In these patents a plastic tube is stretched. An electrode coil having a inner is then slid over the stretched tube, after which the tube, after which the tube is released, allowing it to return to its previous length. Thereafter, a mandrel is inserted into the tubing, compressing the tubing between the mandrel and the conductor coil. The assembly is thereafter heated, allowing the tubing to flow into spaces between the electrode coil to a desired depth.

Other designs for electrode-bearing leads are set forth in U.S. patent application Ser. No. 11/549,284 filed Oct. 13, 2006 by Boser discloses one mechanism for providing such joints.

SUMMARY OF THE INVENTION

The present invention relates to medical electrical leads that include a lead body and at least one tubular electrode sub-assembly positioned over and attached to the lead body. The lead body includes at least one elongated conductive element, such as a cable, that is electrically connected to a coiled electrode of the tubular electrode sub-assembly. The tubular electrode sub-assembly includes a tubular liner and an electrode embedded in the outer surface of the liner. In some embodiments, only a portion of the inner surface of the tubular liner is attached to the lead body in order to improve flexibility of the medical electrode lead in the area occupied by the tubular electrode sub-assembly.

In some embodiments, the tubular electrode sub-assembly may include a thermoplastic tubular liner having an inner surface and an outer surface and an electrode embedded into the outer surface of the thermoplastic tubular liner to depth sufficient to mechanically couple the electrode to the thermoplastic tubular liner, wherein at least a portion of an outer surface of the electrode includes an exposed outer surface proximate the outer surface of the thermoplastic tubular liner. The lead may include one or more selected attachment sites at which the tubular electrode sub-assembly is positioned over and attached to underlying structure of the lead body, wherein the one or more selected attachment sites occupy only a portion of the inner surface of the thermoplastic tubular liner.

The present disclosure also relates to methods of manufacturing medical electrical leads that include manufacturing a tubular electrode sub-assembly by providing a thermoplastic tubular liner and an electrode within a containment cavity, wherein the electrode is located between an outer surface of the thermoplastic tubular liner and an inner surface of the containment cavity, expanding the thermoplastic tubular liner to compress the electrode between the outer surface of the thermoplastic tubular liner and the inner surface of the containment cavity, heating the thermoplastic tubular liner above a forming temperature while the thermoplastic tubular liner is expanded, wherein the electrode embeds into the outer surface of the thermoplastic tubular liner to a depth sufficient to mechanically couple the electrode to the thermoplastic tubular liner, wherein at least a portion of a surface of the electrode comprises an exposed outer surface proximate the outer surface of the thermoplastic tubular liner.

The method of manufacturing the lead may further include positioning an inner surface of the thermoplastic tubular liner of the tubular electrode sub-assembly over underlying structure of a lead body after manufacturing the tubular electrode sub-assembly, wherein the lead body defines a longitudinal axis extending between a proximal end and a distal end of the lead body, and wherein the longitudinal axis extends through the thermoplastic tubular liner; attaching the tubular electrode sub-assembly to the underlying structure of the lead body at one or more selected attachment sites, wherein the one or more selected attachment sites occupy only a portion of an inner surface of the thermoplastic tubular liner; and electrically connecting a conductive element located within an interior of the lead body to the electrode of the tubular electrode sub-assembly.

The principles described herein are applicable to all types of medical electrical leads. For example, the disclosure applies to cardiovascular leads (e.g. high voltage leads, low voltage leads etc.), neurological leads, or other suitable applications. Also, although described with respect to coiled electrodes, other electrode configurations may alternatively be used.

BRIEF DESCRIPTION OF DRAWINGS

Aspects and features of the present invention will be appreciated as the same becomes better understood by reference to the following detailed description of the embodiments of the invention when considered in connection with the accompanying drawings, wherein.

DETAILED DESCRIPTION

In the following detailed description, reference is made to the accompanying figures of the drawing which form a part hereof, and in which are shown, by way of illustration, specific embodiments. It is to be understood that other embodiments may be utilized and structural changes may be made without departing from the scope of the present disclosure.

Figure 1:
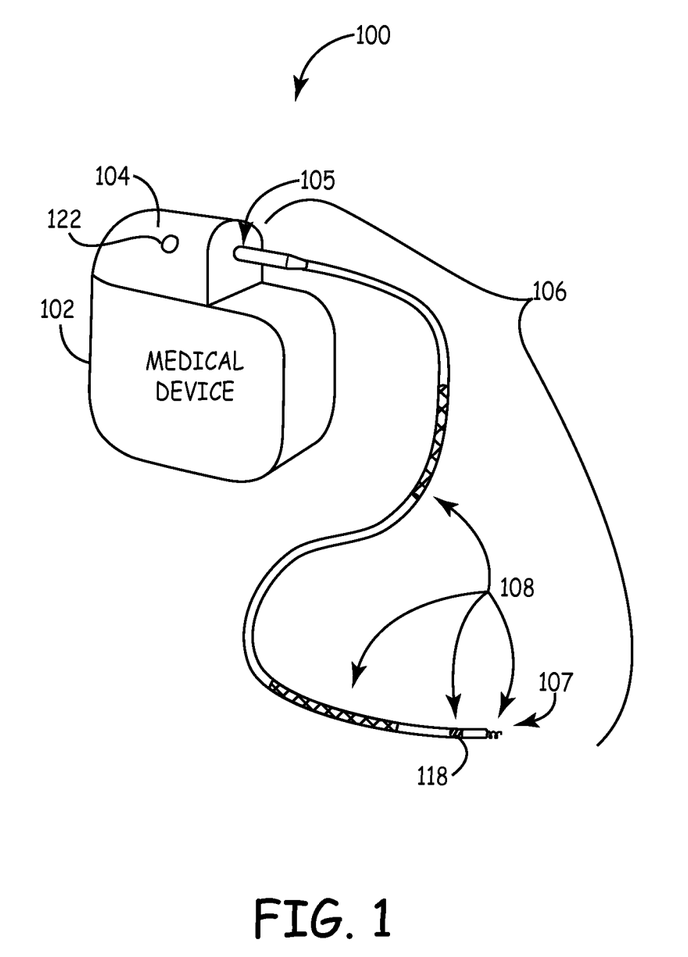
FIG. 1 is a conceptual schematic view of an implantable medical device in which a medical electrical lead extends therefrom.

FIG. 1 depicts a medical device system 100. A medical device system 100 includes a medical device housing 102 having a connector module 104 (e.g. international standard (IS)-1, defibrillation (DF)-1, IS-4 etc.) that electrically couples various internal electrical components housed in medical device housing 102 to a proximal end 105 of a medical electrical lead 106. A medical device system 100 may comprise any of a wide variety of medical devices that include one or more medical lead(s) 106 and circuitry coupled to the medical electrical lead(s) 106. An exemplary medical device system 100 can take the form of an implantable cardiac pacemaker, an implantable cardioverter, an implantable defibrillator, an implantable cardiac pacemaker-cardioverter-defibrillator (PCD), a neurostimulator, a tissue and/or muscle stimulator. IMDs are implanted in a patient in an appropriate location. Exemplary IMDs are commercially available as including one generally known to those skilled in the art, such as the Medtronic CONCERTO™, SENSIA™, VIRTUOSOT™, RESTORE™, RESTORE ULTRA™, sold by Medtronic, Inc. of Minnesota. Non-implantable medical devices or other types of devices may also utilize batteries such as external drug pumps, hearing aids and patient monitoring devices or other suitable devices. Medical device system 100 may deliver, for example, pacing, cardioversion or defibrillation pulses to a patient via electrodes 108 disposed on distal end 107 of one or more lead(s) 106. Specifically, lead 106 may position one or more electrodes 108 with respect to various cardiac locations so that medical device system 100 can deliver electrical stimuli to the appropriate locations.

Figure 2:
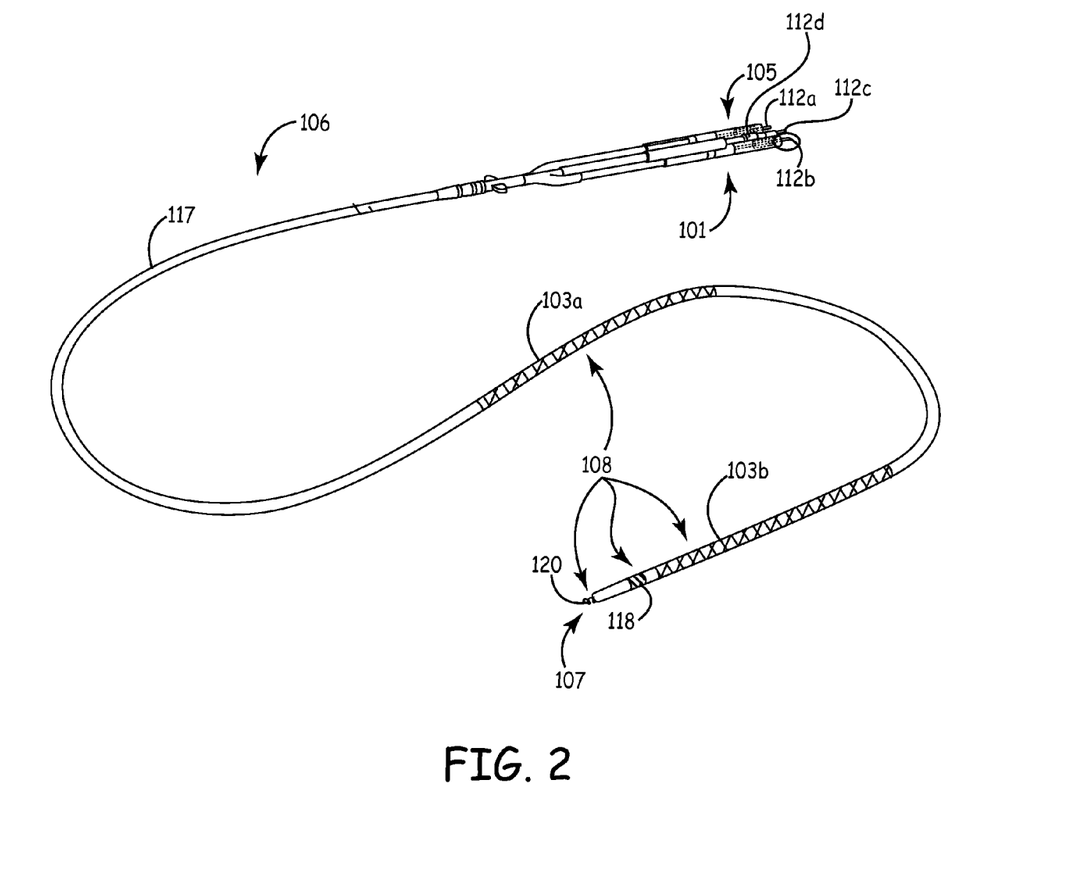
FIG. 2 is a schematic view of a medical electrical lead.

FIG. 2 depicts lead 106. Lead 106 includes a lead body 117 that extends from proximal end 105 to a distal end 107. Lead body 117 can include one or more connectors 101, and one or more jacketed conductive elements 112a-d. A jacket (also referred to as a liner, longitudinal element, coating) extends along and longitudinally around the conductive elements 112a-d and can serve to contain or mechanically constrain one or more conductive elements 112a-d. A jacket can also insulate one or more conductive elements 112a-d. Connector module 104 can contain connectors 122, such as set screws, serve to electrically and mechanically connect conductive elements 112a-d to ports (not shown) of connector module 104. Conductive element 112c (also referred to as a "conductor coil," torque coil", "distal tip conductor") can extend to the distal end 107 and can optionally be coupled to a retractable and/or extendable helical tip. One or more conductive elements 112a,b serve as, or are connected to, defibrillation coils 103a,b that deliver electrical stimuli, when necessary, to tissue of a patient. Lead 106 can also include a conductive element 112d that extends from the proximal end 105 to ring electrode 118 while another conductive element 112c extends from proximal end 105 to tip electrode 120.

Electrically conductive elements that extend along the length of the lead 106 can include coils, wires, coil wound around a filament, cables, conductors or other suitable members. Conductive elements can include platinum, platinum alloys, titanium, titanium alloys, tantalum, tantalum alloys, cobalt alloys (e.g. MP35N, a nickel-cobalt alloy etc.), copper alloys, silver alloys, gold, silver, stainless steel, magnesium-nickel alloys, palladium, palladium alloys or other suitable materials. The electrically conductive elements are typically covered, or substantially covered, longitudinally with a jacket. In yet another embodiment, each conductive element within the lead body 117 is surrounded by a tubular element within the jacket, which can possess a circular or a non-circular cross-section. Any or all of the components within the lead body 117 can exhibit a non-circular cross-section.

Typically, the outer surface of electrodes 108 such as the ring electrode 118, the tip electrode 120, and the defibrillation electrodes 103a,b are exposed or not covered by a jacket or liner so that electrodes 108 can sense and/or deliver electrical stimuli to tissue of a patient. A sharpened distal tip (not shown) of tip electrode 120 may facilitate fixation of the distal end of helically shaped tip electrode 120 into tissue of a patient.

Figure 3A:
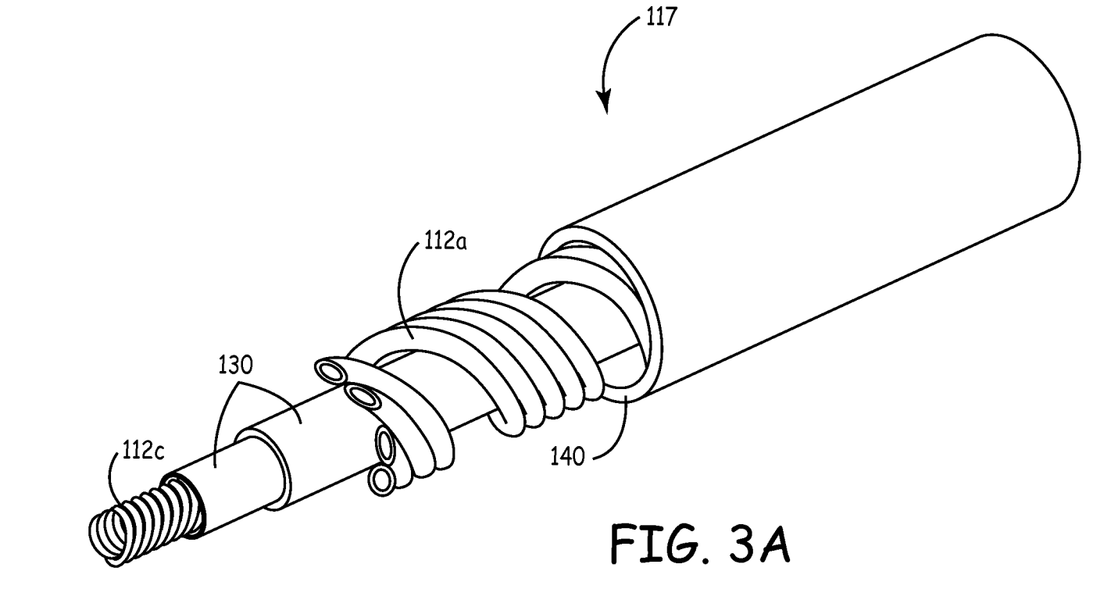
FIG. 3A is a schematic cut-away view of a portion of a medical electrical lead including wrapped conductive elements.
Figure 3B:
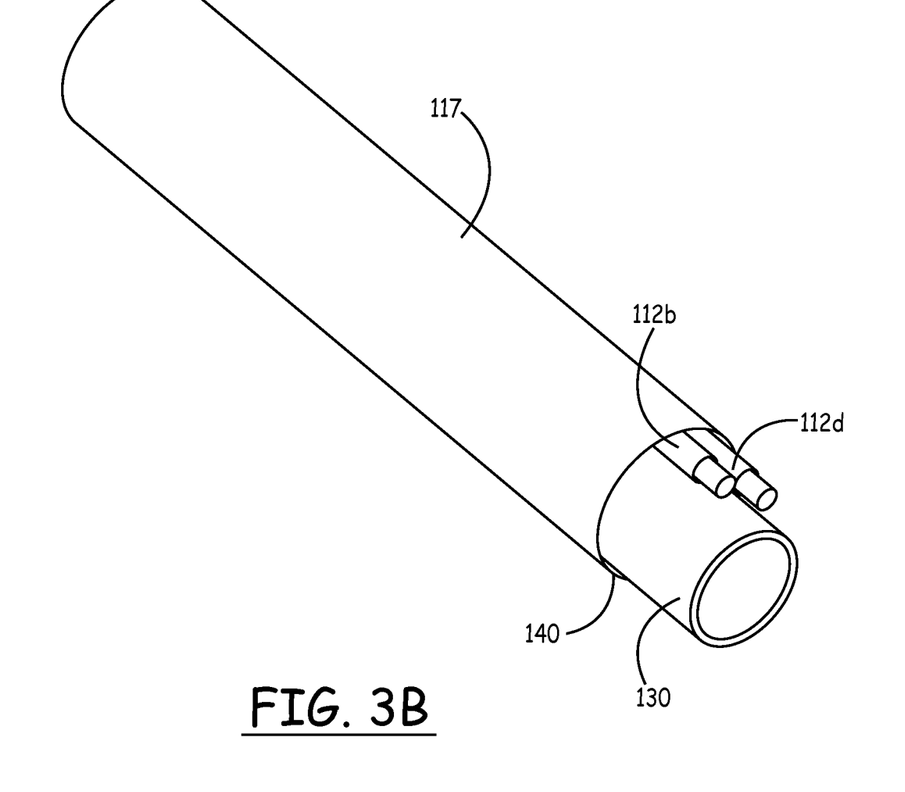
FIG. 3B is a schematic cut-away view of a portion of an alternative medical electrical lead with linearly extending conductive elements.

FIGS. 3A and 3B depict to examples of lead bodies that may be used in connection with the medical electrical leads of the present disclosure. Referring to FIG. 3A, one example of a lead body 117 is depicted that includes one or more conductive elements 112a and 112c that are provided in a wrapped configuration. The depicted lead body 117 also comprises one or more internal jackets 130 with an outer jacket 140 that surrounds the one or more internal jackets 130. FIG. 3B depicts another lead body that includes one or more conductive elements 112b and 112d that extend linearly along the length of the lead body 117. The conductive elements 112b and 112d may be located between an inner structure 130 and an outer jacket 140. In some embodiments, both wrapped and linear conductive elements may be provided in the same lead body. In another embodiment (not pictured) of a lead body that may be used is a multi-lumen tubular structure (symmetric or asymmetric).

Among the electrodes 108, some of the electrodes, such as defibrillation electrodes 103a and 103b, may be provided in the form of coiled electrodes that form a helix, while other electrodes may be provided in different forms. Further, some of the electrodes 108 may be provided in the form of tubular electrode sub-assemblies that can be pre-fabricated and positioned over an existing lead body, where they are attached and where electrical connections with conductive elements within the lead body 117 can be made.

Figure 4:
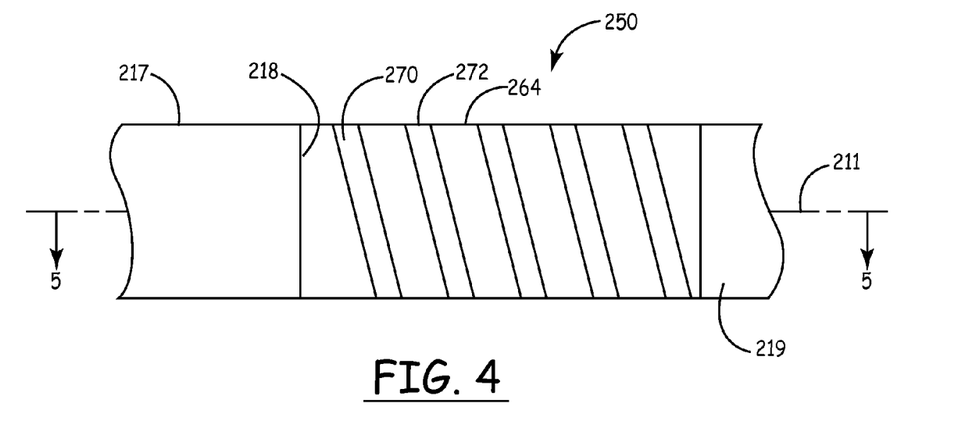
FIG. 4 is a schematic view of a portion of a medical electrical lead that includes a tubular electrode assembly attached thereto.
Figure 5:
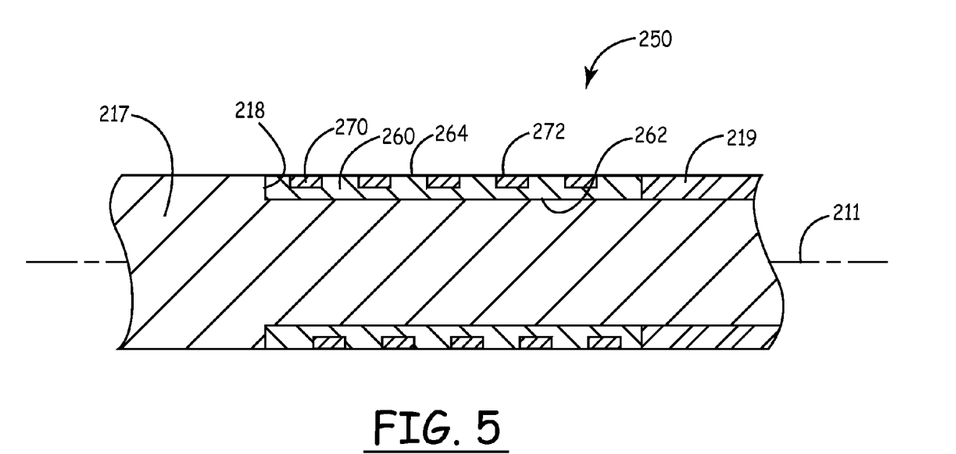
FIG. 5 is a schematic sectional view of the portion of the medical electrical lead of FIG. 4, taken along line 5-5 in FIG. 4.

An example of one such tubular electrode sub-assembly 250 is depicted in FIGS. 4 and 5, where the tubular electrode sub-assembly 250 is positioned over a portion of a lead body 217. The tubular electrode sub-assembly 250 includes a tubular liner 260 and electrode 270 embedded in the outer surface 264 of the tubular liner 260. The electrode 270 is preferably embedded in the outer surface 264 of the tubular liner 260 to a depth that is sufficient to mechanically couple the electrode 270 to the tubular liner 260. At least a portion of the outer surface 272 of the electrode 270 is exposed proximate the outer surface 264 of the tubular liner 260 such that the electrode 270 can be placed in electrical communication with tissue and/or fluids surrounding the tubular electrode sub-assembly 250.

Another optional feature depicted in FIGS. 4 and 5 is that the lead body 217 may be constructed with a variable diameter such that the area in which the tubular electrode sub-assembly 250 is positioned has a reduced size as compared to other portions of the lead body 217. For example, the lead body 217 may include a shoulder 218 as seen in FIG. 5 where the size of the lead body 217 decreases. The diameter of the lead body 217 may be increased on the opposite end of the tubular electrode sub-assembly 250 by optionally including a sleeve 219 or other structure to increase the size of the lead. Such a construction can be used to provide an isodiametric lead, although other constructions could also be used to compensate for the thickness of the tubular electrode sub-assembly 250.

The electrode 270 may, in some embodiments, be formed in the shape of a coil with one or more wraps or coils and using a wire element having a rectangular cross-section as depicted in FIG. 5, although coiled electrodes in other embodiments may be formed using wire elements having any selected shape (e.g., round, oval, elliptical, etc.)

The tubular liner 260 may be located between the electrode 270 and the underlying structure of the lead body 217 over a majority of the inner surface 262 of the tubular liner 260. Exceptions to this may occur where, for example, the electrode is connected to a conductive element extending through the lead body 217. That electrical connection may be made by a variety of techniques, with at least some potentially suitable connection techniques being described in US Patent Application Publication Nos. US 2005/0240252 (Boser et al.); US 2005/0113898 (Honeck et al.); etc.

The tubular liner 260 may alternatively be characterized as preventing contact between the inner surface of the electrode and the underlying structure of the lead body 217 (except where electrical connections may need to be made as described above).

In yet another manner of characterizing the relationship between the tubular liner 260 and the electrode 270 in some embodiments, the tubular liner 260 can be described as optionally having a liner thickness measured radially from the longitudinal axis 211 between the inner surface 262 and the outer surface 264 of the tubular liner 260. The electrode 270 can be described as having an electrode thickness that is measured radially from the longitudinal axis 211. Further, the liner thickness may be greater than the electrode thickness in some embodiments (as depicted, e.g., in FIG. 5).

The tubular liner 260 includes an inner surface 264 that faces the underlying structure of the lead body 217. The tubular electrode sub-assembly 250 is preferably attached to underlying structure of the lead body 217 at one or more selected attachment sites. As discussed herein, the one or more selected attachment sites preferably occupy only a portion of the inner surface 262—in some embodiments, the selected attachment sites may be described as occupying no more than about 50% of the inner surface 262 of the tubular liner 260. By limiting the surface area of attachment between the tubular electrode sub-assembly 250 and the underlying structure of the lead body 217, flexibility of the lead may be improved as compared to a lead in which the entire tubular electrode sub-assembly 250 was attached to the underlying structure of the lead body 217.

Figure 6A:
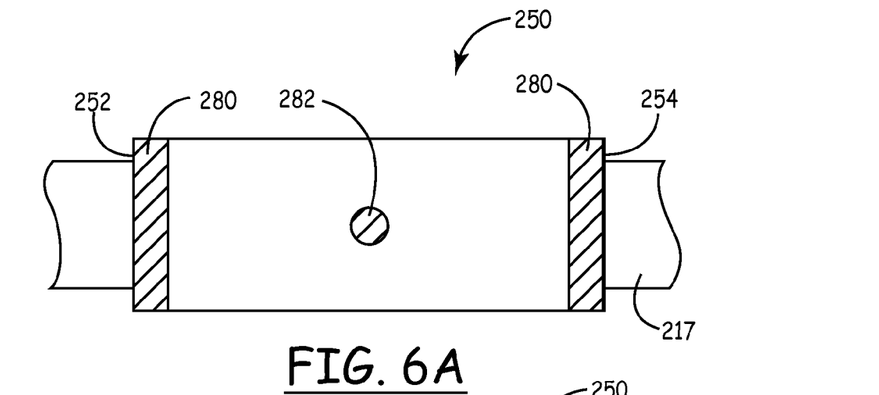
FIG. 6A is a schematic view of a portion of a medical electrical lead including markings to show one arrangement of selected attachment sites where the tubular electrode sub-assembly is attached to the lead body.
Figure 6B:
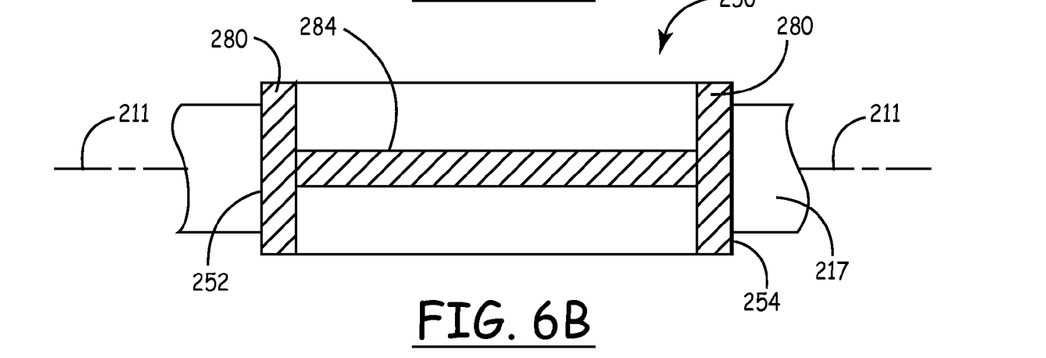
FIG. 6B is a schematic view of a portion of another medical electrical lead including markings to show an alternative arrangement of selected attachment sites where the tubular electrode sub-assembly is attached to the lead body.
Figure 6C:
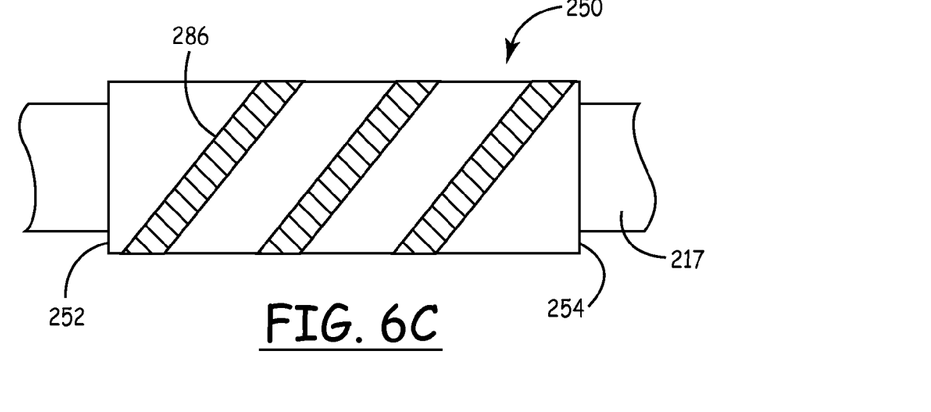
FIG. 6C is a schematic view of a portion of another medical electrical lead including markings to show an alternative arrangement of selected attachment sites where the tubular electrode sub-assembly is attached to the lead body.

FIGS. 6A-6C depict only some of the potentially infinite variations in selection and arrangement of selected attachment sites that may be used to attach the tubular electrode sub-assembly 250 to the underlying lead body 217. The coiled electrode and other features are not depicted in FIGS. 6A-6C for clarity.

In FIG. 6A, the tubular electrode sub-assembly 250 may be attached at its proximal end 252 and its distal end 254 by selected attachment sites 280 that may be in the form of rings around the tubular electrode sub-assembly 250. Although the selected attachment sites 280 at the proximal and distal ends are depicted as continuous rings, they may be provided in any other form, e.g., a group of discrete attachment sites that are arranged around the periphery of the tubular electrode sub-assembly 250 such that a ring structure is formed, etc.

The set of selected attachment sites depicted in FIG. 6A may also optionally include one or more intermediate selected attachment sites 282 positioned between the proximal end 252 and the distal end 254 of the tubular electrode sub-assembly 250. Such an intermediate selected attachment site 282 may be provided in combination with attachment sites 280 at the ends of the tubular electrode sub-assembly 250 or one or more intermediate selected attachment sites 282 may be provided in the absence of attachment sites at the ends of the tubular electrode sub-assembly 250.

One potential alternative arrangement of selected attachment sites is depicted in FIG. 6B in which a selected attachment site 284 in the form of a line is depicted in combination with selected attachment sites 280 at the ends of the tubular electrode sub-assembly 250. Although depicted as a straight line that extends from the proximal end 252 to the distal end 254 of the tubular electrode sub-assembly 250 and that is aligned with the longitudinal axis 211, the line 284 may be shorter and/or the line 284 may not be aligned with the longitudinal axis 211. Further, the attachment site 284 may be provided in combination with attachment sites 280 at the ends of the tubular electrode sub-assembly 250 (as depicted) or one or more such lines may be provided in the absence of attachment sites at the ends of the tubular electrode sub-assembly 250.

Another potential alternative arrangement of selected attachment sites is depicted in FIG. 6C in which a selected attachment site 286 is provided in the form of a helix that extends around the tubular electrode sub-assembly 250 and proceeds along its length between the proximal end 252 and the distal end 254. Although the selected attachment site 286 is depicted as a continuous structure, it may be provided in any other form, e.g., a group of discrete attachment sites that are arranged around and along the tubular electrode sub-assembly 250 such that a helical structure is formed, etc. Additional selected attachment sites may also be provided in combination with a helical selected attachment site 286.

In still another alternative, limiting the area occupied by the attachment sites between the tubular electrode sub-assembly 250 and the underlying structure of the lead body may not be used if, for example, the tubular electrode sub-assembly 250 is attached to the underlying structure of the lead body by an attachment agent that has a lower modulus than the material used to construct the liner 260 of the tubular electrode sub-assembly 250. For example, using a silicone medical adhesive to attach the inner surface of the liner 260 to the underlying structure of the lead body 217 may provide sufficient compliance to provide enhanced flexibility in the lead such that the attachment agent (e.g., silicone adhesive, etc.) may occupy more than about 50% of the surface are occupied by the tubular electrode sub-assembly 250. In some embodiments, the attachment agent may be provided over substantially all of the interface between the inner surface of the liner 260 and the underlying structure of the lead body 217.

As discussed herein, the electrode 270 is embedded in the outer surface 264 of the tubular liner 260. One potential method for manufacturing a tubular electrode sub-assembly having such a construction is depicted and will be described in connection with FIG. 7, which is a sectional view of the process.

Figure 7:
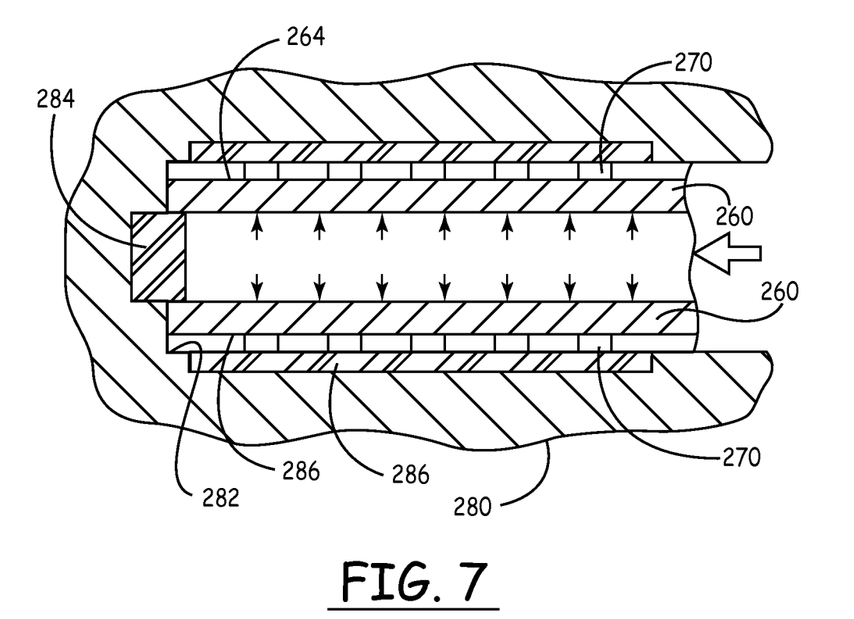
FIG. 7 is a schematic sectional view of a process for forming a tubular electrode sub-assembly with an embedded electrode.

The embedment process may preferably be accomplished within a containment cavity formed in a containment structure 280. The containment structure 280 may be provided in any suitable form such as a mold, a tube, etc., that is capable of providing a cavity that can contain the tubular electrode sub-assembly 250 during the manufacturing process described herein.

In the depicted method, a tubular liner 260 is provided within the interior of an electrode 270 which may, optionally, be a coiled electrode. Both the tubular liner 260 and the electrode 270 are located within a cavity of the containment structure 280, where the cavity is defined by the inner surface 282 of the containment structure 280. The exact order in which the components are placed in the containment cavity may not be important, so long as all of the components can be accurately placed within the containment cavity, for example, the electrode 270 may be placed in the containment structure 280 first, with the tubular liner 260 being inserted after the electrode 270. In one potential alternative, the electrode 270 may be placed over the outer surface 264 of the tubular liner 260 before the electrode and the tubular liner 260 are placed in the containment structure 280 as an assembly. Regardless of the order of placement, the end result has the electrode 270 located between the outer surface 264 of the liner 260 and the inner surface 282 of the containment structure 280.

With the components in place, the liner 260 may be expanded such that the electrode 270 is compressed between the outer surface 264 of the liner 260 and inner surface 282 of the containment cavity. The expansion may be accomplished by any suitable technique or combination of techniques, e.g., mechanically, pneumatically, hydraulically, etc. that is capable of providing pressure on the liner 260 radially outward from the interior of the liner 260. In some embodiments, the pressure may be uniformly applied to the entire inner surface 262 of the liner 260, although this may or may not be required.

In one embodiment, the expansion may be accomplished by introducing an inflation fluid into the interior of the tubular liner 260 such that the coiled electrode 270 is compressed between the outer surface 264 of the liner 260 and the inner surface 282 of the containment structure 280. One end of the tubular liner 260 may preferably be sealed to prevent the flow of fluid out of the tubular liner 260, e.g., a plug 284 is inserted into one end of the tubular liner 260, the liner 260 may be clamped off, etc. At the same time, the tubular liner 260 is also heated such that the internal pressure forces the material of the liner to flow around and at least partially embed the electrode 270 in the outer surface 264 of the liner 260 (see, e.g., FIGS. 4 and 5). The heating and inflation may be accomplished by introducing a heated inflation fluid into the liner 260. Potentially suitable inflation fluids may include air, carbon dioxide, and other gases, as well as liquids such as, e.g., water, oil, etc. In some instances, the inflation fluid may be provided in a bladder or other containment vessel to reduce or prevent contamination of the tubular electrode sub-assembly 250 by the inflation fluid.

In some methods, the inner surface 282 of the containment structure 280 may be heated to enhance the embedment process.

The containment structure 280 may optionally include or be composed of compliant material 286 along the inner surface 282 of the containment structure that can conform to the outer surface of the electrode 270. Such compliant material 282 may seal off or mask at least a portion of the outer surface of the electrode 270 during the embedment process. This may be useful if, e.g., the electrode 270 is made using rounded wires or elements, rectangular wires or elements, etc.

The compliant material is selected to seal off and prevent the thermoplastic material from coating the intended exposed surface of the electrode assembly. Examples include, but are not limited to, silicones, fluoropolymers, and fluoroelastomers. For example, such materials include low consistency silicones (e.g., those available under the trade designations MED-4719 or MED-4755 from NuSil), liquid silicone rubber (LSR) (such as Dow Corning's Q7-4850 or NuSil's MED-4850), Dyneon's THV (a polymer of tetrafluoroethylene, hexafluoropropylene and vinylidene fluoride), Daikin's T-530 fluoroelastomer. Specific types of silicones may be more appropriate if features need to be molded in (i.e. an LSR molding grade of silicone could be used), or if non-planar contours, shapes, or fine features need to be sealed-off (i.e., a lower durometer silicone could be used).

It is desirable that the compliant material be stable when subjected to the processing temperatures and not adhere to the thermoplastic material. For instance, a relatively low durometer silicone tubing or silicone mold insert can be used to comply to the electrode surface with pressure and effectively seal-off from ingress of the thermoplastic material. Alternatively, a fluoroelastomer such as Dyneon's THV or Daikin's T-530 could be used. A variation would include heat-shrink fluoropolymer tubing such as fluorinated ethylene propylene (FEP), ethylene tetrafluoroethylene (ETFE), or polytetrafluoroethylene (PTFE) to seal-off and define the electrode assembly outer diameter, i.e., this would be contained within the mold cavity, oven, or other equipment to provide the necessary heat to flow the thermoplastic material.

The conditions under which the embedment is accomplished will vary based on a variety of factors such as, e.g., the composition of the liner, the thickness and size of the liner, the dimensions of the electrode, the time over which the pressure and/or heat are applied, etc. In some embodiments, the expansion device (e.g., expandable tube, inflation fluid, etc.) may be heated to a temperature that approaches the melting temperature of the materials used to form the liner or to some other temperature at which the liner material can reflow such that the electrode can be embedded as described herein. If, for example, the liner 260 is constructed of a polyurethane silicone copolymer, suitable temperatures for an inflation fluid may range from about 150 to about 250 degrees Celsius at pressures that may range from about 30 to about 100 psi.

Figure 8:
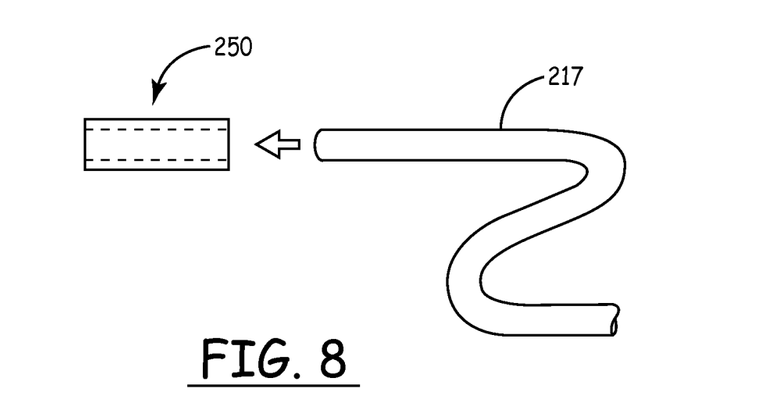
FIG. 8 is a schematic view of a process for placing a tubular electrode sub-assembly onto a lead body.

After the embedment process is complete, the tubular electrode sub-assembly can be removed from the containment structure 280 and processed such that it is in condition to be placed over a lead body as depicted in FIG. 8 and attached thereto in one or more selected attachment sites as described herein. Such processing to prepare the tubular electrode sub-assembly 250 for attachment to a lead body 217 may include, trimming the tubular electrode sub-assembly 250 to a selected length, preparing the ends or other portions of the coiled electrode for attachment to a conductive element within the lead body 217, etc.

Attachment of the tubular electrode sub-assembly 250 to a lead body 217 may be accomplished using any suitable technique or combination of techniques. In some embodiments, the tubular electrode sub-assembly 250 may be attached to the lead body 217 by welding the material of the liner 260 to the lead body 217. Such welding may be performed using any suitable technique or combination of techniques, e.g., ultrasonically, thermally, chemically (using, e.g., solvents), etc.

Another potential technique for providing the selected attachment sites between the tubular electrode sub-assembly 250 and the lead body 217 may be through the use of adhesive. Exemplary adhesive may include silicones, urethanes, flouropolymers etc. The adhesives could include those activated via thermal, UV light, chemical, moisture, and solvent-based methods.

Another potentially optional process that may be used is to backfill or overcoat the tubular electrode sub-assembly 250 before and/or after positioning it on a medical electrical lead with a hardenable organic polymeric material that has a relatively low modulus (i.e., low stiffness, low durometer) for good flexibility of the final assembly, and has a relatively low viscosity (e.g., "pre-cure" viscosity) for good mold-filling properties. The material used to backfill may be a thermoset or a thermoplastic material. Examples include silicones, polyimides, epoxies, polyurethanes, polyurethanes with surface-modifying end groups (SME), polyurethane silicone block copolymers (e.g., a thermoplastic silicone polyether urethane available under the designation PurSil), ethylene tetrafluoroethylene (ETFE), polytetrafluoroethylene (PTFE), polyvinylidine difluoride (PVDF), Dyneon's THV (a polymer of tetrafluoroethylene, hexafluoropropylene and vinylidene fluoride), Daikin's T-530 fluoroelastomer, and other fluoropolymers and fluoropolymer elastomers, polyethylenes, and polyesters.

The materials used to form the tubular liners of the tubular electrode sub-assemblies may be selected from a wide variety of thermoplastic materials that have a relatively low modulus (i.e., low stiffness, low durometer) for good flexibility of the final assembly, and has a relatively low viscosity for good mold-filling properties. Examples include polyurethanes, polyurethanes with surface-modifying end groups (SME), polyurethane silicone block copolymers (e.g., a thermoplastic silicone polyether urethane available under the designation PurSil), fluoropolymers and fluoroelastomers (including ethylene tetrafluoroethylene (ETFE), polytetrafluoroethylene (PTFE), polyvinylidine difluoride (PVDF), Dyneon's THV (a polymer of tetrafluoroethylene, hexafluoropropylene and vinylidene fluoride), Daikin's T-530 fluoroelastomer, and other fluoropolymers and fluoroelastomers), polyethylenes, and polyesters. Note that e-beam irradiated ETFE or other fluoropolymers and fluoroelastomers are referred to herein as "thermoplastics" although they cannot be reflowed with heat after crosslinking. In some embodiments, a thermoplastic material, such as polyurethane silicone block copolymers (such as PurSil silicone polyether urethane), a polyurethane, a polyurethane with surface-modifying end groups, and ETFE), can be used for the tubular liner.

Fabrication of an electrode assembly using a thermoplastic material typically involves the simultaneous application of heat and pressure to cause the material to flow and fill the void spaces. The conditions needed (e.g., time, temperature, pressure), depend on the selection of the material and can be readily determined by one of skill in the art. For example, the temperature is related to the melt flow index of the material and has to be sufficient enough to flow the material adequately with the pressure applied. Increasing the temperature increases the fluidity (i.e., decreases viscosity) of the material and allows it to flow easier, as does increasing pressure.

The electrodes used in the tubular electrode assemblies may be selected from a wide variety of electrically conductive biocompatible materials (including, but not limited to, titanium, stainless steel, tantalum, platinum, etc. and combinations thereof (e.g., platinum-iridium clad tantalum, etc.)) that can be formed to take on any selected shape, e.g., a coiled helical shape, etc.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used herein, "a," "an," "the," "at least one," and "one or more" are used interchangeably. Thus, for example, a leg clamp may refer to one or more leg clamps unless otherwise indicated.

The term "and/or" means one or all of the listed elements or a combination of any two or more of the listed elements.

The complete disclosure of the patents, patent documents, and publications identified herein are incorporated by reference in their entirety as if each were individually incorporated.

The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. A medical electrical lead comprising:
   a lead body that comprises a length between proximal end and a distal end, wherein the lead body defines a longitudinal axis extending between the proximal end and the distal end;
   a conductive element located within an interior of the lead body and extending along the longitudinal axis for at least a portion of the length of the lead body;
   a tubular electrode sub-assembly positioned over the exterior surface of the lead body such that the longitudinal axis extends through the tubular electrode sub-assembly, wherein the tubular electrode sub-assembly comprises:
      a thermoplastic tubular liner comprising an inner surface and an outer surface,
      an electrode embedded into the outer surface of the thermoplastic tubular liner to depth sufficient to mechanically couple the electrode to the thermoplastic tubular liner, wherein at least a portion of an outer surface of the electrode comprises an exposed outer surface proximate the outer surface of the thermoplastic tubular liner;
   one or more selected attachment sites at which the tubular electrode sub-assembly is positioned over and attached to underlying structure of the lead body, wherein the one or more selected attachment sites occupy only a portion of the inner surface of the thermoplastic tubular liner;
   an electrical connection within the medical electrode lead between the electrode and the conductive element.

2. The medical electrical lead of claim 1, wherein the thermoplastic tubular liner is located between the electrode and the underlying structure of the lead body over a majority of the inner surface of the thermoplastic tubular liner.

3. The medical electrical lead of claim 1, wherein the thermoplastic tubular liner prevents contact between an inner surface of the electrode and the underlying structure of the lead body.

4. The medical electrical lead of claim 1, wherein the thermoplastic tubular liner has a liner thickness measured radially from the longitudinal axis between the inner surface and the outer surface of the thermoplastic tubular liner, and wherein the electrode has an electrode thickness measured radially from the longitudinal axis, and further wherein the liner thickness is greater than the electrode thickness.

5. The medical electrical lead of claim 1, wherein the one or more selected attachment sites comprise the proximal end and the distal end of the thermoplastic tubular liner.

6. The medical electrical lead of claim 1, wherein the one or more selected attachment sites comprise the proximal end of the thermoplastic tubular liner, the distal end of the thermoplastic tubular liner, and an intermediate location between the proximal end and the distal end of the thermoplastic tubular liner.

7. The medical electrode lead of claim 1, wherein the one or more selected attachment sites occupy no more than about 50% of the inner surface of the thermoplastic tubular liner.

8. The medical electrical lead of claim 1, wherein at least one selected attachment site of the one or more selected attachment sites is in the form of a line extending along at least a portion of a length of the thermoplastic tubular liner between a proximal end and a distal end of the thermoplastic tubular liner.

9. The medical electrical lead of claim 8, wherein the line extends from the proximal end of the thermoplastic tubular liner to the distal end of the tubular liner.

10. The medical electrical lead of claim 8, wherein the line is aligned with the longitudinal axis.

11. The medical electrical lead of claim 8, wherein the line comprises a helix formed around the longitudinal axis.

12. The medical electrical lead of claim 1, wherein the electrode comprises a coiled electrode in the form of helix.

13. The medical electrical lead of claim 1, wherein the thermoplastic tubular liner comprises an organic polymeric material selected from the group consisting of polyurethanes, polyurethanes with surface-modifying end groups, polyurethane silicone block copolymers, fluoropolymers, fluoroelastomers, polyethylenes, and polyesters.

14. The medical electrode lead of claim 1, wherein at least one selected attachment site of the one or more selected attachment sites comprises a welded bond between the thermoplastic tubular liner and the lead body.

15. The medical electrical lead of claim 1, wherein at least one selected attachment site of the one or more selected attachment sites comprises an adhesive located between the inner surface of the thermoplastic tubular liner and the external surface of the lead body.

16. The medical electrode lead of claim 5, wherein the one or more selected attachment sites occupy no more than about 50% of the inner surface of the thermoplastic tubular liner.

17. The medical electrode lead of claim 6, wherein the one or more selected attachment sites occupy no more than about 50% of the inner surface of the thermoplastic tubular liner.

18. The medical electrode lead of claim 8, wherein the one or more selected attachment sites occupy no more than about 50% of the inner surface of the thermoplastic tubular liner.

19. The medical electrode lead of claim 14, wherein the one or more selected attachment sites occupy no more than about 50% of the inner surface of the thermoplastic tubular liner.

20. The medical electrode lead of claim 15, wherein the one or more selected attachment sites occupy no more than about 50% of the inner surface of the thermoplastic tubular liner.

21. The medical electrical lead of claim 5, wherein the thermoplastic tubular liner prevents contact between an inner surface of the electrode and the underlying structure of the lead body.

22. The medical electrical lead of claim 6, wherein the thermoplastic tubular liner prevents contact between an inner surface of the electrode and the underlying structure of the lead body.

23. The medical electrical lead of claim 8, wherein the thermoplastic tubular liner prevents contact between an inner surface of the electrode and the underlying structure of the lead body.

24. The medical electrical lead of claim 14, wherein the thermoplastic tubular liner prevents contact between an inner surface of the electrode and the underlying structure of the lead body.

25. The medical electrical lead of claim 15, wherein the thermoplastic tubular liner prevents contact between an inner surface of the electrode and the underlying structure of the lead body.

* * * * *